(12) United States Patent
Zayas et al.

(10) Patent No.: US 8,124,770 B2
(45) Date of Patent: Feb. 28, 2012

(54) FLUORESCENT CELLULAR MARKERS

(76) Inventors: Beatriz Zayas, San Juan, PR (US);
Osvaldo Cox, Humacao, PR (US)

( * ) Notice: Subject to any disclaimer, the term of this patent is extended or adjusted under 35 U.S.C. 154(b) by 293 days.

(21) Appl. No.: 12/416,174

(22) Filed: Apr. 1, 2009

(65) Prior Publication Data

US 2010/0256378 A1 Oct. 7, 2010

(51) Int. Cl.
*C07D 513/04* (2006.01)
*C07D 471/04* (2006.01)

(52) U.S. Cl. ............................ 546/62; 546/70

(58) Field of Classification Search .................... 546/62, 546/70

See application file for complete search history.

(56) References Cited

U.S. PATENT DOCUMENTS 4,590,275 A * 5/1986 Cox et al. ...................... 546/62

OTHER PUBLICATIONS

Zayas, B. et al.: Comparison of the nucleic acid covalent binding capacity of two nitro-substituted benzazolo[3,2-a]quinolinium salts upon enzymatic reduction. Toxicology in Vitro, vol. 21, pp. 1155-1164, 2007.*

* cited by examiner

*Primary Examiner* — Charanjit Aulakh (57) ABSTRACT

A synthesis procedure for benzazolo[3,2-a]quinolinium chloride salts and the inclusion of amino-substituent and nitro-substituent resulting in four compounds such as NBQ-38 (7-Ethyl-3-nitrobenzimidazolo[3,2-a]quinolinium Chloride), NBQ-95(2-Chloro-10-methyl-3-nitrobenzothiazolo[3,2-a]quinolinium chloride), ABQ-38(3-amino-7-ethylbenzimidazo [3,2-a]quinolinium chloride), and ABQ-95 (3-amino-2-chloro-10-methylbenzothiazolo[3,2-a]quinolinium chloride) wherein said procedures provides an increment in the compounds biological activity. The compounds are further used for intra cellular binding, cytotoxicity on malignant cells through apoptosis activation mediated by mitochondrial damage and caspases 3 and 7 activation, cellular organelles binding and damage, and a marker due to the auto-fluorescent properties.

21 Claims, 10 Drawing Sheets

Figure 1

| Series | Name | X | $R_1$ | $R_2$ | Formula | MW (g/mol) | IC50 |
|---|---|---|---|---|---|---|---|
| 2 | ABQ-38 | NEt | 3-$NH_2$ | H | $C_{17}H_{16}ClN_3$ | 297.78 | 32 µM |
| 2 | NBQ-38 | NEt | 3-$NO_2$ | H | $C_{17}H_{14}ClN_3O_2$ | 327.77 | 36 µM |
| 1 | ABQ-95 | S | 2-Cl, 3-$NH_2$ | 10-Me | $C_{16}H_{12}Cl_2N_2$ | 335.95 | 28 µM |
| 1 | NBQ-95 | S | 3-$NO_2$, 2-Cl | 10-Me | $C_{16}H_{10}Cl_2N_2O_2$ | 365.25 | 51 µM |

| II | X | $R_1$ | $R_2$ | % Yield[a] | Mp (°C) |
|---|---|---|---|---|---|
| a | S | 2,3,5-triCl | H | 38 | 150-152 |
| b | S | 2-Cl | 5-$CH_3$ | 62 | 126-127 |
| c | S | 2-Cl, 5-$NO_2$ | 5-$CH_3$ | 60 | 196-197 |
| d | S | 2-Cl, 5-$NH_2$ | 5-$CH_3$ | 99 | 154-156 |
| e | S | α-$CH_3$, 2-Cl, 5-$NO_2$ | H | 65 | 155-156 |
| f | S | 2-Cl, 5-$NO_2$ | 5-$CH_2Br$ | 81[b] | 212-215 |
| g | S | 2,3,6-triCl | 6-Br | 36[c] | 177-179 |
| h | S | 2,4-diCl, 5-$NO_2$ | 5-$CH_3$ | 66 | 198-200 |
| i | S | 2,4-diCl, 5-$NO_2$ | H | 77 | 168-170 |
| j | S | 2-Cl, 5-$NO_2$ | 5-F | 47 | 203-204 |
| k | S | 2,3-diF | H | 67 | 130-133 |
| l | S | 2-Cl, 5-$NO_2$ | 5-OH | 99[d] | 240-242 |
| m | S | 2-Cl, 5-$NO_2$ | 5-OAc | 50 | 198-202 |
| n | S | 2-Cl, 5-$NO_2$ | 5-$OCH_3$ | 70 | 220-222 |
| o | S | 2-Cl, 4-$N(CH_3)_2$ | H | 65 | 143-146 |
| p | S | 2-Cl, 6-$NO_2$ | H | 52[e] | 82-83 |
| q | S | 2,3,6-triCl | H | 56[e,f] | 148-150 |
| r | S | 2,6-diCl | 6-$OCH_3$ | 70[e] | 119-121 |
| s | S | 2,6-diCl | 5-$CH_3$ | 65[e] | 144-145 |
| t | NEt | 2-Cl, 3-$NO_2$ | H | 61 | 150-152 |
| v | NEt | 2-Cl, 3-$NH_2$ | H | 99 | 171-173 |

Figure 4

X = S, Se, O or N-alkyl

Figure 5

| No. NBQ | X | R₁ | R₂ | R₃ | % Yield[a] |
|---|---|---|---|---|---|
| 76 | S | 4-Cl | H | H | 50 |
| 81 | S | 2-Cl, 3-NO₂ | H | H | 16 |
| 82 | S | 2,3-diCl | H | H | 44 |
| 91 | S | 3-NO₂ | H | 10-CH₃ | 73 |
| 95 | S | 2-Cl, 3-NO₂ | H | 10-CH₃ | 41[d] |
| 96 | S | 3-NO₂ | H | 10-OAc | 23 |
| 97 | S | 3-NO₂ | H | 10-OCH₃ | 75 |
| 99 | S | 3-NO₂ | H | 10-F | 45 |
| 101 | S | 3-NO₂ | H | 10-OH | 53 |
| 103 | S | 3-NO₂ | H | 10-CH₂Br | 23 |
| 104 | S | 3-NO₂ | 6-CH₃ | H | 30[b] |
| 106 | S | H | H | 10-CH₃ | 54[c] |
| 108 | S | 4-Cl | H | 10-CH₃ | 65[c] |
| 113 | S | 4-Cl | H | 9-OCH₃ | 67[c] |

[a] The yields are reported after freezing drying of the aqueous water extracts. [b] This compound was prepared following Method 2, its yield following Method 3 was 7.0%. [c] This compound was prepared following Method 3. [d] This compound was prepared following Method 4

Figure 6

| No | X | R₁ | R₂ | Formula |
|---|---|---|---|---|
| NBQ-1 | S | H | H | $C_{15}H_{10}ClNS$ |
| NBQ-2 | S | 3-NO$_2$ | H | $C_{15}H_9ClN_2O_2S$ |
| NBQ-6 | S | 3-NO$_2$ | 2,3-OCH$_2$O- | $C_{16}H_{10}ClNO_2S$ |
| NBQ-25 | S | 3-NO$_2$ | 9-OMe | $C_{16}H_{11}ClN_2O_3S$ |
| NBQ-26 | S | 3-NO$_2$ | 9-F | $C_{15}H_8ClFN_2O_2S$ |
| NBQ-27 | S | 3-NO$_2$ | 9-Br | $C_{15}H_8BrClN_2O_2S$ |
| NBQ-35 | S | 3-NO$_2$ | 6-Cl | $C_{15}H_8Cl_2N_2O_2S$ |
| NBQ-36 | S | 3-NO$_2$ | 9-Cl | $C_{15}H_8Cl_2N_2O_2S$ |
| NBQ-37 | S | 2-NO$_2$ | H | $C_{15}H_9ClN_2O_2S$ |
| NBQ-57 | S | 3-Br | H | $C_{15}H_9BrClNS$ |
| NBQ-73 | S | H | 9-Br | $C_{15}H_9BrClNS$ |
| NBQ-74 | S | 3-NO$_2$ | 8,9-C$_4$H$_4$- | $C_{19}H_{11}ClN_2O_2S$ |
| NBQ-76 | S | 4-Cl | H | $C_{15}H_9Cl_2NS$ |
| NBQ-81 | S | 3-NO$_2$,2-Cl | H | $C_{15}H_8Cl_2N_2O_2S$ |
| NBQ-82 | S | 3,4-di-Cl | H | $C_{15}H_8Cl_3NS$ |
| NBQ-84 | S | 3-NO$_2$ | 9,10-diOMe | $C_{17}H_{13}ClN_2O_4S$ |
| NBQ-85 | S | 3-NO$_2$ | 9,10-OCH2O- | $C_{16}H_9ClN_2O_4S$ |
| NBQ-86 | S | 3-NO$_2$ | 8,9-C$_4$H$_4$- | $C_{19}H_{11}ClN_2O_2S$ |
| NBQ-91 | S | 3-NO$_2$ | 10-Me | $C_{16}H_{11}ClN_2O_2S$ |
| NBQ-92 | S | 3,4-di-Cl | 9-Br | $C_{15}H_7BrCl_3NS$ |
| NBQ-93 | S | 1,3-di-Cl | H | $C_{15}H_8Cl_3NS$ |
| NBQ-94 | S | 3,4-di-Cl | 10-Me | $C_{16}H_{10}Cl_3NS$ |
| NBQ-95 | S | 3-NO$_2$, -Cl | 10-Me | $C_{16}H_{10}Cl_2N_2O_2$ |
| NBQ-96 | S | 3-NO$_2$ | 10-OAc | $C_{17}H_{11}ClN_2O_4$ |
| NBQ-97 | S | 3-NO$_2$ | 10-OMe | $C_{16}H_{11}ClN_2O_3S$ |
| NBQ-99 | S | 3-NO$_2$ | 10-F | $C_{15}H_8ClFN_2O_2S$ |
| NBQ101 | S | 3-NO$_2$ | 10-OH | $C_{15}H_9ClN_2O_3S$ |
| NBQ-103 | S | 3-NO$_2$ | 10-CH$_2$Br | $C_{16}H_{10}BrClN_2O_2S$ |
| NBQ-104 | S | 3-NO$_2$ | 6-Me, H | $C_{16}H_{11}ClN_2O_2S$ |
| NBQ-106 | S | H | 10-Me | |
| NBQ-108 | S | 4-Cl | 10-Me | |
| NBQ-113 | S | 4-Cl | 9-OMe | |
| ABQ-2 | S | 3-NH$_2$ | H | $C_{15}H_{11}ClN_2S$ |
| ABQ-91 | S | 3-NH$_2$ | 10-Me | $C_{16}H_{13}ClN_2S$ |
| ABQ-95 | S | 2-Cl, 3-NH$_2$ | 10-Me | $C_{16}H_{12}Cl_2N_2$ |
| ABQ-25 | S | 3-NH$_2$ | 9-OMe | $C_{16}H_{13}ClN_2OS$ |

Figure 7

| No. | X | R₁ | R₂ | Formula | MW |
|---|---|---|---|---|---|
| NBQ-38 | NEt | 3-$NO_2$ | H | $C_{17}H_{14}ClN_3O_2$ | 327.77 |
| NBQ-47 | NMe | 3-$NO_2$ | H | $C_{16}H_{12}ClN_3O_2$ | 313.74 |
| NBQ-48 | $NCH_2Ph$ | 3-$NO_2$ | H | $C_{23}H_{16}ClN_3O_2$ | 401.85 |
| NBQ-49 | NiPr | 3-$NO_2$ | H | $C_{18}H_{16}ClN_3O_2$ | 341.80 |
| NBQ-50 | N-nBu | 3-$NO_2$ | H | $C_{19}H_{18}ClN_3O_2$ | 355.82 |
| NBQ-51 | NEt | H | H | $C_{17}H_{15}ClN_2$ | 282.77 |
| NBQ-58 | $MeSCH_2$ | 3-$NO_2$ | H | $C_{17}H_{14}ClN_3O_2$ | 359.83 |
| NBQ-59 | MeCH=CH | 3-$NO_2$ | H | $C_{18}H_{14}ClN_3O_2$ | 339.78 |
| NBQ-72 | $nC_{15}H_{31}$ | 3-$NO_2$ | H | $C_{30}H_{40}ClN_3O_2$ | 510.12 |
| NBQ-75 | -$(CH_2)_4CN$ | 3-$NO_2$ | H | $C_{20}H_{17}ClN_4O_2$ | 380.83 |
| NBQ-77 | -$(CH_2)_2OBn$ | 3-$NO_2$ | H | $C_{24}H_{20}ClN_3O_3$ | 433.89 |
| NBQ-83 | -$(CH_2)_3Br$ | 3-$NO_2$ | H | $C_{18}H_{15}BrClN_3O_2$ | 420.69 |
| NBQ-88 | -$(CH_2)_2OH$ | 3-$NO_2$ | H | $C_{17}H_{14}ClN_3O_3$ | 343.77 |
| NBQ-89 | $MeOCH_2$ | 3-$NO_2$ | H | $C_{17}H_{14}ClN_3O_3$ | 343.77 |
| NBQ-98 | c-$C_6H_{11}$- | 3-$NO_2$ | H | $C_{21}H_{20}ClN_3O_2$ | 381.86 |
| ABQ-38 | NEt | 3-$NH_2$ | H | $C_{17}H_{16}ClN_3$ | |
| ABQ-48 | NBn | 3-NH2 | H | $C_{23}H_{18}ClN_3$ | |

Figure 8

| NBQ-3 | O | 3-$NO_2$ | H | $C_{15}H_9ClN_2O_3$ |
|---|---|---|---|---|

Figure 9

| NBQ-4 | Se | 3-NO2 | H | C15H9ClN2O2Se |
|---|---|---|---|---|
| NBQ-87 | Se | 3-NO2 | 10-OMe | C16H11ClN2 O3Se |

FLUORESCENT CELLULAR MARKERS

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The present invention relates to the synthesis and biological activity of nitro-substituted benzazolo[3,2-a]quinolinium chloride salts (NBQs) and amino-substituted benzazolo[3,2-a]quinolinium chloride salts (ABQs), more particularly to a synthesis procedure for producing benzazolo[3,2-a]quinolinium chloride salts and amino-substituted benzazolo[3,2-a] quinolinium chloride salts that exhibit distinctive biological activity and fluorescent properties.

2. Discussion of the Background

The scientific community continuously needs to apply cellular markers when studying how cells or subjects respond or behave to a given internal or external stimulus. Some of these stimuli include, but are not limited to, drug treatments, therapies and natural disease processes.

U.S. Pat. No. 4,590,275 to Cox et al. (Cox '275), discloses the preparation of benzazolo[3,2-a]quinolinium chloride salts (BQSs) which shows cytotoxic, antitumor and antiviral activity. However Cox '275 fails to disclose the synthesis of amino-substituted benzazolo[3,2-a]quinolinium (ABQs) compounds, wherein said ABQs possess fluorescent properties applicable in the identification of cellular organelles and biological activities applicable for therapeutic applications. The fluorescent property assists the user to identify cellular organelles making the compounds excellent markers for research, diagnostic or treatment. Some of the biological activities include, but are not limited to, cellular toxicity, mitochondria damage and apoptosis induction on tumor cell lines in culture.

Also Cox '275 discloses different methods for the synthesis of several compounds, however the disclosed methods do not limit the excitation by irradiation of the compounds in order to avoid unwanted reactions resulting in unwanted characteristics and properties. Further the BQSs were isolated as the perchlorate salt through its precipitation by addition of an aqueous perchloric acid or a saturated sodium perchlorate solution avoiding isolating the pure BQS's.

SUMMARY OF THE INVENTION

The present invention overcomes the limitations of the synthesized benzazolo[3,2-a]quinolinium chloride salts as presented by Cox '275 et al. and discloses a synthesis procedure that increases the biological activity and greater selectivity toward tumor cells providing the auto fluoresce in cell cultures, inducing cytotoxity through apoptosis, binding to cellular organelles and caspaces activation on human malignant or normal cells in culture.

The selection of the compounds are part of benzazolo[3,2-a]quinolinium salts, (BQS), that had been synthesized in four series of compounds:

Series 1 (X=S), are benzothiazolo[3,2-a]quinolinium chlorides or perchlorates that incorporate a fused benzothiazole in rings C and D;

Series 2 (X=NR) are benzimidazolo[3,2-a]quinolinium chlorides that incorporate a fused benzimidazole moiety in rings C and D;

Series 3 (X=O), are benzoxazolo[3,2-a]quinolinium chlorides or perchlorates that incorporate a benzoxazole ring in rings C and D;

Series 4 (X=Se), are benzoselenazolo[3,2-a]quinolinium chlorides that incorporate a benzoselenazole moiety in rings C and D.

Compounds in series 1-4 are further characterized by the inclusion of a nitro- or amino-substituent in ring A, these are identified as NBQs and ABQs, respectively. Even when all these series are presented the invention is particularly directed to the synthesis and biological activity of four BQSs (NBQ-38, ABQ-38, NBQ-95 and ABQ-95), belonging to series 1 and 2.

First, the present invention discloses a compound, such as amino-substituted benzazolo[3,2-a]quinolinium showing (1) intra cellular binding; (2) cytotoxicity on malignant cells through apoptosis activation mediated by mitochondrial damage and caspases 3 and 7 activation; (3) cellular organelles binding and damage. Also the compound has shown auto-fluorescent properties in contact with cells. These fluorescent properties allow a clear indication of the interaction with cellular organelles serving as a fluorescence marker in research or as a therapeutic marker or a diagnostic marker in clinical studies. It could be applied to monitor the presence and concentrations of microorganisms in the environment since they also possess cellular organelles to which these fluorescent compounds can bind. Further the ABQs display increased selectivity against cancer cells as compared to NBQs in series 1 and 2.

Second, the present invention discloses the synthesis of nitro- and amino-substituted benzothiazolo[3,2-a]quinolinium salts I causing cell death via an apoptosis mechanism, interaction with macro organelles such as mitochondria and DNA, activation of caspases 3 and 7, and the formation of 8-2-dG adducts upon bioreduction in the presence of XO/HX. Also synthesized nitro-substituted benzothiazolo[3,2-a] quinolinium salts I have shown the ability to selectively target hypoxic cells and the capacity for inhibition of topoisomerase II in tumor cells.

Third the present invention discloses an improved procedure for the synthesis of benzothiazolo[3,2-a]quinolinium salts I (BQs).

Therefore one of the objectives of the present invention is to provide a compound showing intra cellular binding, cytotoxicity on malignant cells through apoptosis activation mediated by mitochondrial damage and caspases 3 and 7 activation, cellular organelles binding and damage and auto fluorescence.

Another object of the invention is to provide a synthesized nitro-substituted benzothiazolo[3,2-a]quinolinium salts I (NBQs) causing cell death via an apoptosis mechanism, interaction with macro organelles such as mitochondria and DNA, activation of caspases 3 and 7, and the formation of 8-2-dG adducts upon bioreduction in the presence of XO/HX.

Another objective of the invention is to provide a synthesized nitro-substituted benzothiazolo[3,2-a]quinolinium salts that allows the identification of tumor or abnormal tissues.

Another objective of the invention is to provide a new improved method for the synthesis of BQs which is more compatible with the biological systems.

Another objective of the invention is to provide a synthesis method of BQs that avoids unwanted reactions.

Another objective of the invention is to provide a synthesis method of BQs that improves performance of the compounds.

Another objective of the present invention is to provide a compound suitable as an anti-cancer therapeutic agent.

A further objective of the present invention is to provide fluorescent BQ analogs that serve as therapeutic markers since they can indicate organs or tissues where the BQs have interacted with.

The invention itself, both as to its configuration and its mode of operation will be best understood, and additional objects and advantages thereof will become apparent, by the following detailed description of a preferred embodiment taken in conjunction with the accompanying drawing.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings, which are incorporated herein, constitute part of the specifications and illustrate the preferred embodiment of the invention.

FIG. 7 a table showing Benzothiazolo[3,2-a]quinolinium Chloride Derivatives Series 1.

DESCRIPTION OF THE PREFERRED EMBODIMENT

Figure 1:
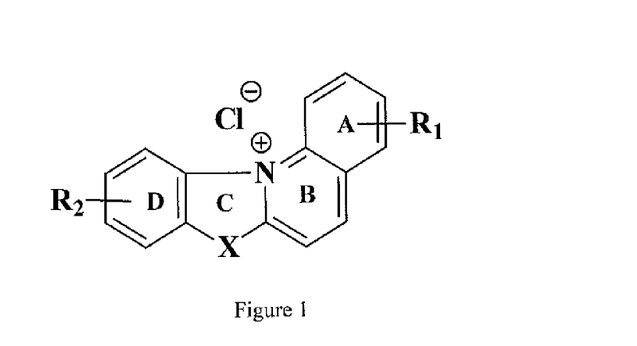
FIG. 1 shows the general Structure of the present invention.
Figure 2:
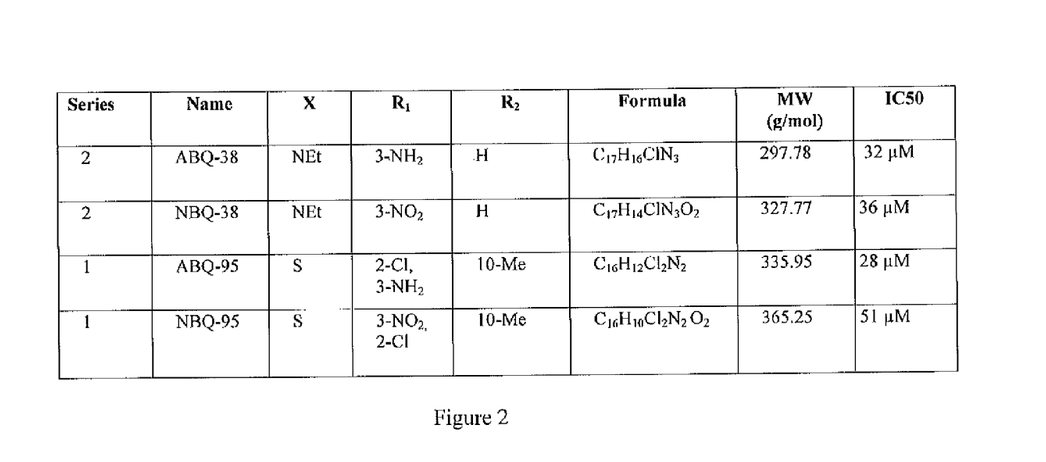
FIG. 2 shows a table of the Chemical Formulas of developed BQSs.
Figure 3:
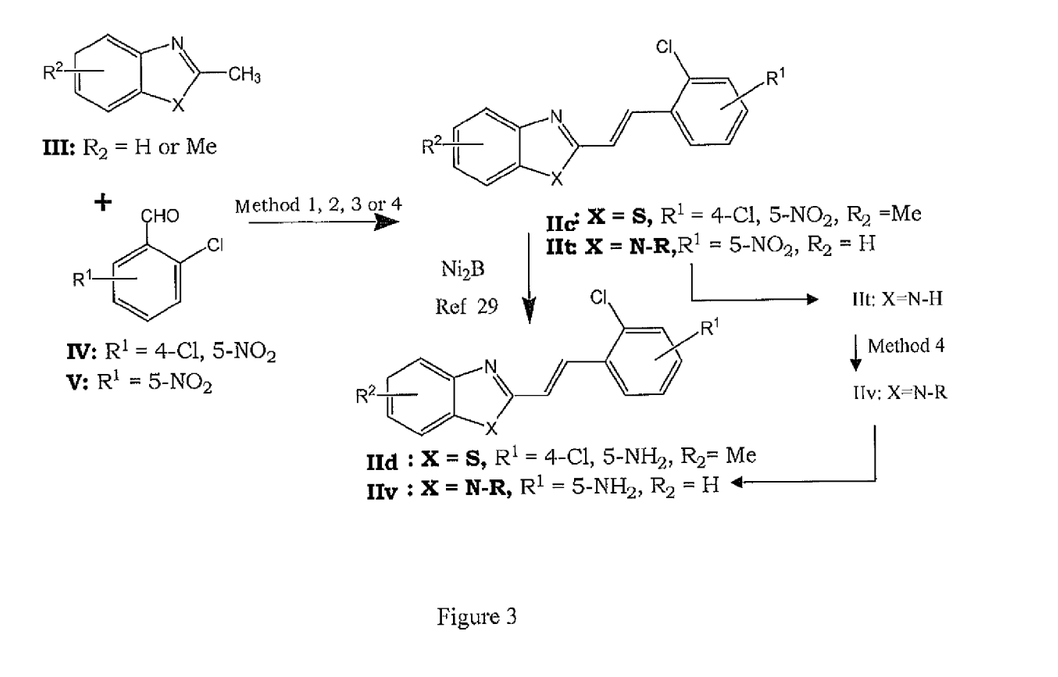
FIG. 3 Synthetic methodologies for the preparation of (E)-2-styrylbenzazole derivatives II
Figure 4:
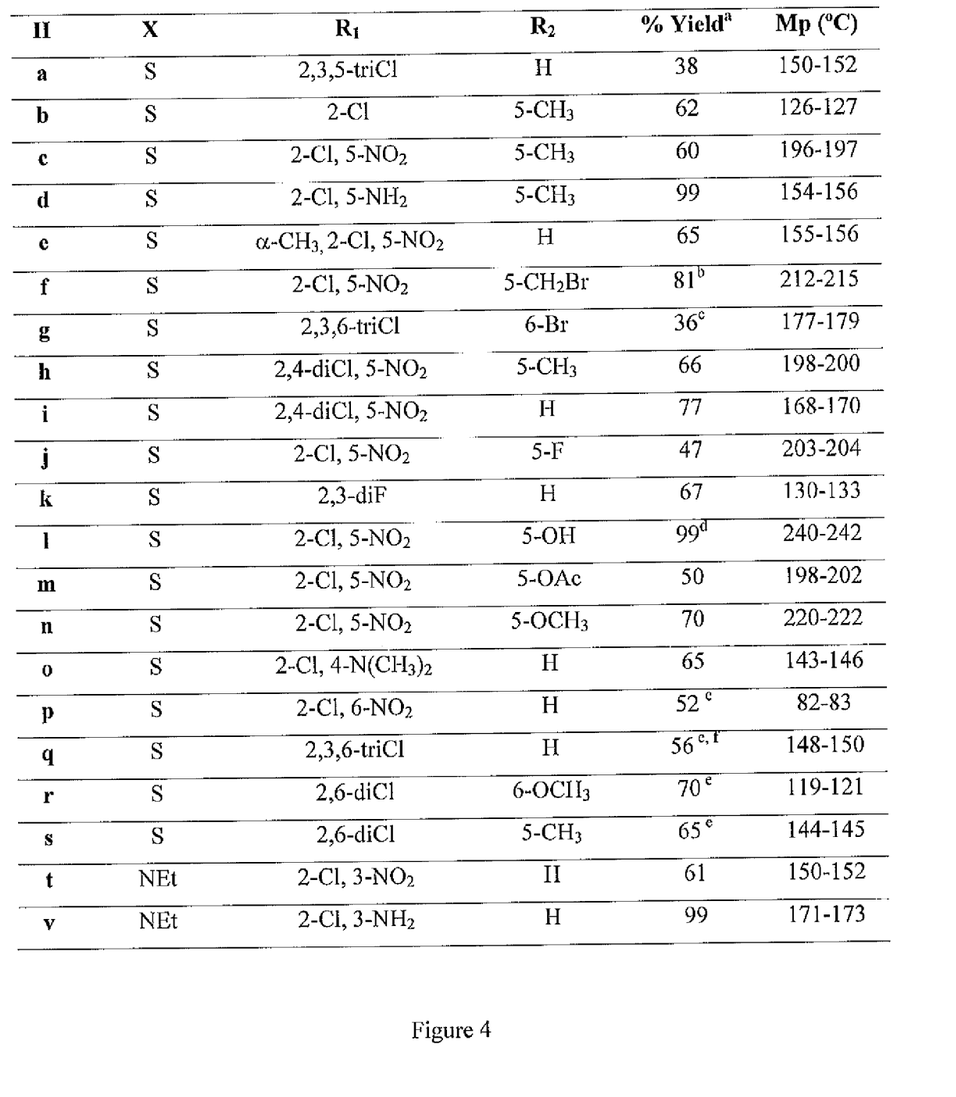
FIG. 4 shows a table of the Chemical Formulas (E)-2-styrylbenzazole derivatives II
Figure 5:
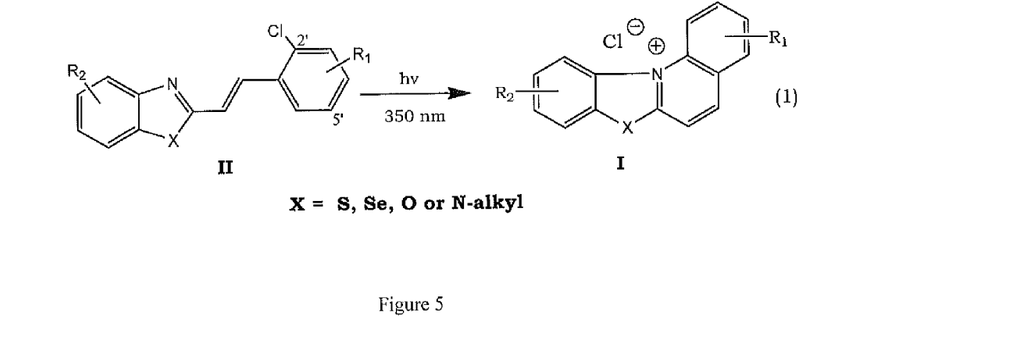
FIG. 5 shows the synthesis of BQS (I) by the photoinduced cyclization of II.
Figure 6:
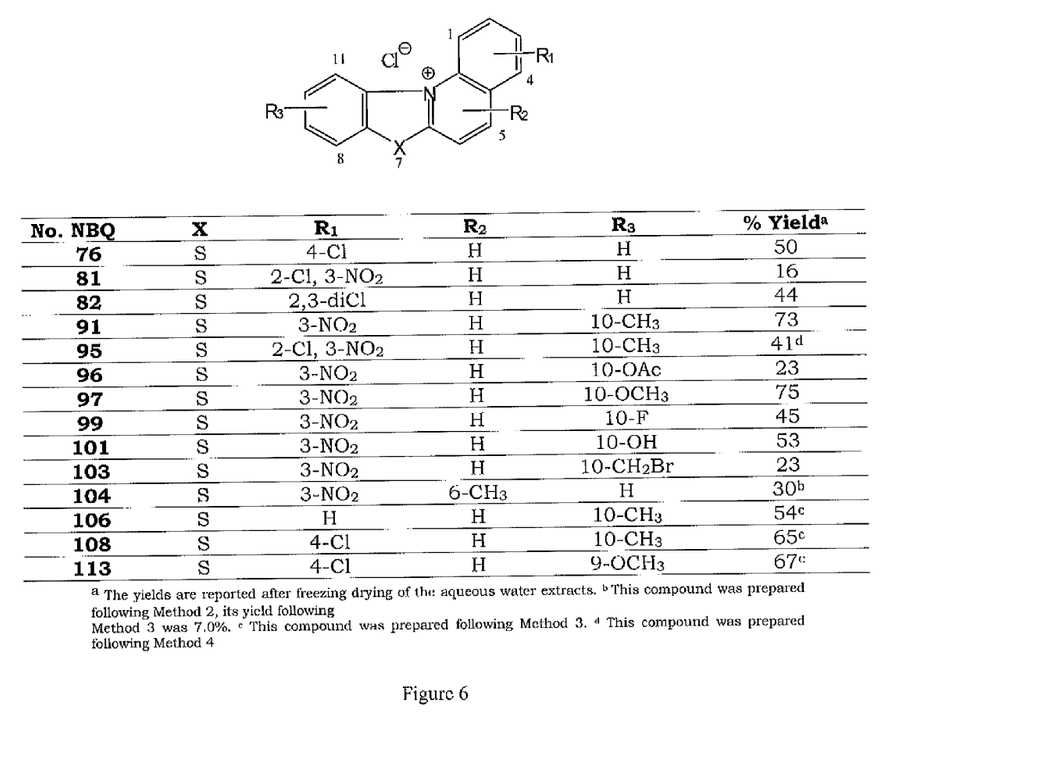
FIG. 6 synthesis of new benzazolo[3,2-a]quinolinium chloride derivatives using new methods.

FIG. 1 shows a general structure of the synthesized NBQs and ABQs. The present invention is particularly directed to the synthesis and biological activity of four BQSs (NBQ-3S, ABQ-38, NBQ-95 and ABQ-95), as shown in FIG. 2. The synthetic sequence commences with the synthesis of a nitro substituted 2-(2-chlorostyryl)benzothiazole II and a particular methodology followed by reduction of the nitro group with hydrazine using nickel boride as catalyst, as shown in FIG. 3 and FIG. 4. Further the photo-induced cyclization of II through a procedure gives I in acceptable yields. The result is the Synthesis benzazolo[3,2-a]quinolinium chlorides as shown in FIG. 5, FIG. 6 and FIG. 7.

Figure 8:
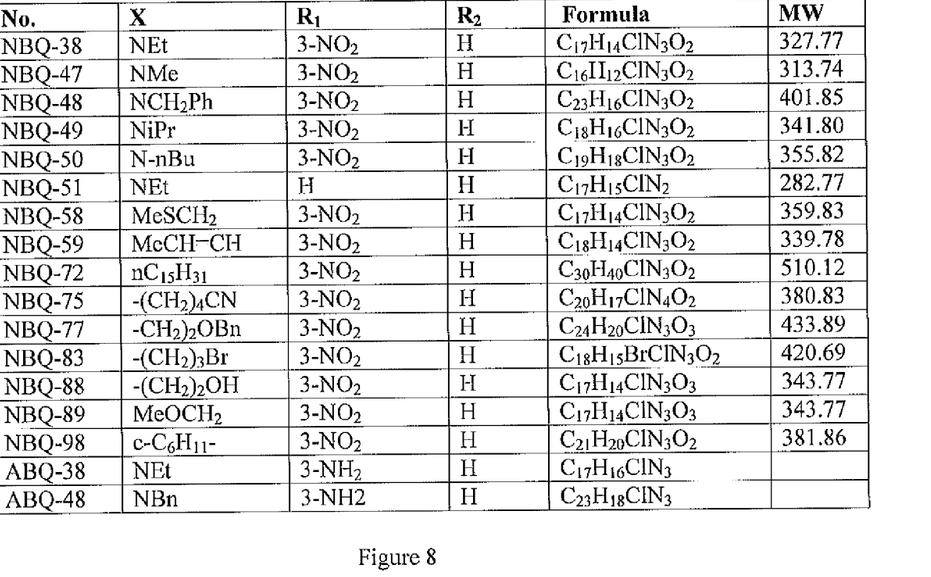
FIG. 8 a table showing Benzimidazolo[3,2-a]quinolinium Chlorides Derivatives, Series 2.
Figure 9:
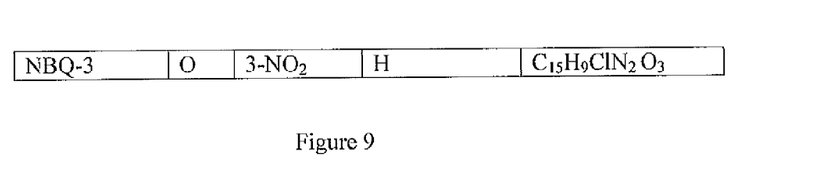
FIG. 9 a table showing Benzoxalo[3,2-a]quinolinium Chloride Derivatives, Series 3.
Figure 10:
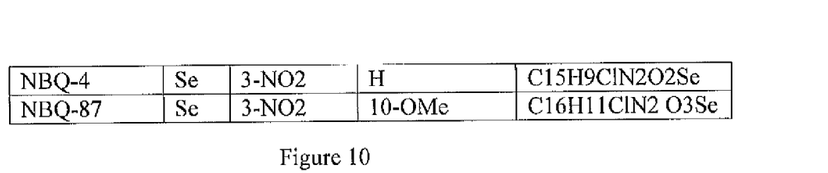
FIG. 10 a table showing Benzoselenazolo[3,2-a]quinolinium Chloride Derivatives, Series 4.

Four series were synthetized, wherein a series 1 (X=S), as shown in FIG. 7, comprises benzothiazolo[3,2-a]quinolinium chlorides or perchlorates that incorporate a fused benzothiazole in rings C and D; series 2 (NR), as shown in FIG. 8, comprises benzimidazolo[3,2-a]quinolinium chlorides that incorporate a fused benzimidazole moiety in rings C and D; series 3 (X=O), as shown in FIG. 9, comprises benzoxazolo[3,2-a]quinolinium chlorides or perchlorates that incorporate a benzoxazole ring in rings C and D; finally series 4 (X=Se), as shown in FIG. 10, comprises benzoselenazolo[3,2-a] quinolinium chlorides that incorporate a benzoselenazole moiety in rings C and D. Series 1-4 are further characterized by the inclusion of a nitro- or amino-substituent in ring A, these are identified as NBQs and ABQs, respectively. The chosen ones from NBQs and ABQs tables were NBQ-38, ABQ-38, NBQ-95 and ABQ-95 obtained from series 1 and 2, as shown in FIG. 2.

The particular methodology or method comprises several measurements and apparatus used in order to perform the synthesis of the compounds. In the instant case the several processes were carried out in pre-dried glassware (2 h, 125° C.) under an open atmosphere, unless stated otherwise. The irradiations were conducted at room temperature between 23°-25° C. using a Rayonet Photochemical Reactor fitted with 350 nm lamps. Melting points were determined in a capillary tube using a Melt-Temp apparatus. The $^1H$ and $^{13}C$ nmr spectra were recorded on a spectrometer, such as a General Electric QE-300 (using a 5 mm C/H dual probe) operating at an observation frequency of 300.15 and 75.48 MHz for $^1H$ and $^{13}C$, respectively and equipped with a software that processes and analyses the data acquired from observation such as Nicolet 1280 data system and a 293-C pulse programmer or on a spectrometer such as Bruker DRX500 (using a 5 mm broad band probe) operating at an observable frequency of 500.13 and 125.77 MHz for $^1H$ and $^{13}C$, respectively. The proton data were referenced to either tetramethylene (TMS) at δ 0.0 ppm, chloroform ($CDCl_3$) at δ 7.26 ppm or methyl sulfoxide (DMSO-d6) at δ 2.49 ppm. The $^{13}C$ nuclei were referenced to the center peak of the 1:1:1 multiplet of deuteriochloroform at δ 77.0 ppm or the multiplet of hexadeuteriomethyl sulfoxide was assigned at δ 39.5 ppm.

Infrared Spectra were recorded on a Nicolet Series 6000 FT-IR spectrometer. High Resolution Mass Spectra (HRMS) spectra were recorded on a fluorescence spectroscope, such as a FISON instrument, VG Auto Spect Series using a Direct Insertion Probe (DIP). The HRMS parameters were as follows: Electron-impact: 70 eV; resolution: 1000 ppm; temperature ramp: 100-400° C. (30° C./min). Thin Layer Chromatography (TLC) were developed on polyester supported silica gel of 0.25 cm thickness with fluorescent indicator and visualized with ultraviolet light (254 nm) Elemental analyses were performed by Atlantic Microlab.

In addition, the compounds were exposed to nuclear magnetic resonance studies wherein the processes were carried out at a temperature between 23-25° C. using 5 mm NMR sample tubes. The solvents used were DMSO-$d_6$ and $CDCl_3$ and the quantity of sample ranged from 30 to 150 mg, all dissolved in approximately 0.50 to 0.75 mL of the corresponding deuterium-substituted solvent. The conditions of measurement of the $^1$H and $^{13}$C nmr spectra were as follows: pulse width, 8.75 μs (90°) and 9.60 μs (90°), respectively; spectral width 3311 Hz and 14705 Hz, respectively; data points 16 K and 32 K, respectively.

The COSY spectra were recorded using a pulse sequence such as the sequence described by Bax and Freeman. The spectral widths were 3311 Hz in both dimensions ($F_1$, $F_2$). The spectra were either collected as 256×1 K block of data in Bruker DRX500 or with 16-24 acquisitions per block and 0.1 s between acquisitions in General Electric QE-300, and was processed to a final 512×512 real point matrix (zerofilling the $F_1$ dimension) using sine bell multiplications in each dimension followed by symmetrization of the final data matrix.

All the Heteronuclear Multiple Quantum Coherence (HMQC) and Heteronuclear Multiple Bond Correlations (HMBC) experiments were performed on a Bruker DRX500 NMR spectrometer. The spectra were acquired from a 256×4 matrix with 96 accumulations performed for each $t_1$ and processed to a final 512×512 real point matrix (zerofilling the $F_1$ dimension) using cosine and sine squared multiplication in $F_1$ and $F_2$ dimensions, respectively. The delay times were 3.0 ms ($1/2\ J_{CH}=\Delta_1$), to suppress one-bond responses, and 50 ms ($1/''\ J_{CH}=\Delta_2$) for evolution of long range coupling (10 Hz).

The BQS, NBQs and ABQs, were synthesized using several methods. However the inclusion of amino-substituent and nitro-substituent in ring A were performed after the synthesis of (E)-2-Styrlbenzazlole and Benzazlol[3,2-a]quinolinium Chlorides (BQS).

The Synthesis of (E)-2-Styrlbenzazlole, as shown in FIG. 3 and FIG. 4, has at least four different methods wherein each method comprises:

1. Method 1

An equimolar mixture of the corresponding 2-chlorosubstituted benzaldehyde and the corresponding 2-methylbenzazole derivatives were dissolved in a molar excess of acetic anhydride and refluxed for 18 to 24 h. The solution was allowed to cool at a temperature between 23°-25° C. and the precipitated solid was filtered, washed with acetic anhydride, or cold 2:1 hexane/acetone mixture. Recrystallization of the precipitate from an organic aprotic solvent such as acetone, hexane/acetone 1:1 mixture; cyclohexane or toluene gave the desired product.

2. Method 2

An equimolar solution of 2-methylbenzothiazole and the corresponding 2-chloro-6-substituted benzaldehyde in DMSO (10 mL) was added in one step a 50% sodium hydroxide solution (3.0 mL) with constant stirring at a temperature between 23°-25° C. The formation of a solid was observed immediately, and the mixture was allowed to stir for an additional 5-15 min. After adding water, the reaction mixture was stirred for an approximately 5 min. Vacuum filtration and recrystallization from toluene or acetone gave the desired product.

3. Method 3

An equimolar mixture of the corresponding 2-chlorosubstituted benzaldehyde and the corresponding 2-methylbenzazole derivatives was dissolved in a molar excess of acetic anhydride and refluxed for 18 to 24 h. The solution was allowed to cool at a temperature between 23°-25° C. and the precipitated solid was filtered, washed with acetic anhydride, or cold 2:1 hexane/acetone mixture. Recrystallization of the precipitate from an organic aprotic solvent such as acetone, hexane/acetone 1:1 mixture, cyclohexane or toluene gave the desired product.

In order to hinder 2-chloro-6-substituted benzaldehydes the process includes an extension consisting of a technique involving condensation such as reflux. During the reflux comprises the equimolar mixture with a small amount of the 2-methylbenzozale derivative (0.2 equiv.) in boiling acetic anhydride for prolonged reaction time between 48 to 168 h. The reaction progress is monitored by TLC and $^1$H NMR spectroscopy.

4. Method 4

This method was developed for the preparation of (E)-1-substituted-2-(2-chloro-5-nitrostyryl)benzimidazole (II) where the R group is sensitive to acid conditions. Specifically, these compounds were prepared by alkylation of the corresponding (E)-2-styrylbenzimidazo-1-yl anion with an alkyl halide (R—X)]. A 60% sodium hydride dispersion in mineral oil (2.2 equivalents) was added to dry DME and stirred with cooling in an ice bath water under Argon atmosphere. The (E)-1H-2-(2-chloro-5-nitrostyryl)benzimidazole (1.0 equivalents) was then added in one portion. Once the addition of the (E)-styrylbenzimidazole (II) had been completed, the reaction mixture was left stirring at 23°-25° C. for 30 min. The alkylating agent (1.5 equivalents per equivalent of the (E)-styrylbezimidazole) was then slowly added at room temperature and the reaction mixture left stirring under a nitrogen atmosphere for 6-24 h. At the end of this time, the resulting reaction mixture was cooled in an ice-water bath and water was added. The resulting precipitate was filtered under vacuum, washed using 1:1 acetone/hexane mixture and air-dried.

The Synthesis of Benzazlol[3,2-a]quinolinium Chlorides are performed using at least four different methods, as shown in FIG. 6, wherein each method comprises:

1. Method 1.

A permeable vessel to a wavelength of 350 nm lamps was used. In the instant case, the selected reaction vessel was a Pyrex tube (40×6×0.3 cm). The irradiations were conducted using a Rayonet photochemical reactor equipped with 350 nm lamps, instead of a 450 W-Hanovia mercury vapor lamp as light source. It is important to understand that the specificity of the irradiation is to avoid unwanted reactions. A 0.2-1.0 g sample of the corresponding (E)-2-(2-chlorostyryl)benzazole (II) dissolved in 150-250 mL of 3:1 benzene:dioxane mixture was irradiated for 10-18 h intervals. After each interruption, the solution was filtered to remove part of the product. The solid material on the filter paper was obtained in a pure form. The rest of the product remains in the walls of the tube, was extracted with distilled water (ca. 15 mL). The filter paper was also washed with water to remove the water-soluble product. The combined water extracts from several irradiations were filtered and subject to freeze-drying to isolate the pure BQS. Before reuse, the irradiation vessel was sequentially washed with acetone, ethanol, sulfuric acid (1.0 M), water, dilute sodium carbonate solution (10%), distilled water and acetone. Finally, it was dried in an oven for no less than 24 h.

2. Method 2.

A permeable vessel to a wavelength of 350 nm lamps was used. In the instant case the reaction vessel was a Pyrex tube (40×6×0.3 cm). The irradiations were conducted using a Rayonet photochemical reactor equipped with 350 nm lamps, instead of a 450 W-Hanovia mercury vapor lamp as light source. A 0.2-1.0 g sample of the corresponding (E)-2-(2-chlorostyryl)benzazole (II) dissolved in 150-250 mL of 2:1:1 benzene:bromobenzene:dioxane mixture before the irradiation. After each interruption, the solution was filtered to remove part of the product. The solid material on the filter paper was obtained in a pure form. The rest of the product remains in the walls of the tube, was extracted with distilled water (ca. 15 mL). The filter paper was also washed with water to remove the water-soluble product. The combined water extracts from several irradiations were filtered and subject to freeze-drying to isolate the pure BQS. Before reuse, the irradiation vessel was sequentially washed with acetone, ethanol, sulfuric acid (1.0 M), water, dilute sodium carbonate solution (10%), distilled water and acetone. Finally, it was dried in an oven for not less than 24 h.

3. Method 3.

A vessel permeable to a wavelength of 350 nm lamps was used. In the instant case, the reaction vessel was a Pyrex tube (40×6×0.3 cm). The irradiations were conducted using a Rayonet photochemical reactor equipped with 350 nm lamps, instead of a 450 W-Hanovia mercury vapor lamp as light source. A 0.2-1.0 g sample of the corresponding (E)-2-(2-chlorostyryl)benzazole (II) dissolved in 150-250 mL of 3:1 benzene:dioxane mixture was first degassed with Argon and then irradiated for 5-18 h. Between intervals of 4-5 h the solution is filtered to remove part of the product. The solid material on the filter paper was obtained in a pure form. The rest of the product remains in the walls of the tube, were extracted with distilled water (ca. 15 mL). The filter paper was also washed with water to remove the water-soluble product. The combined water extracts from several irradiations were filtered and subject to freeze-drying to isolate the pure BQS. In the original procedure the BQSs were isolated as the perchlorate salt through its precipitation by addition of an aqueous perchloric acid or a saturated sodium perchlorate solution. Before reuse, the irradiation vessel was sequentially washed with acetone, ethanol, sulfuric acid (1.0 M), water, dilute sodium carbonate solution (10%), distilled water and acetone. Finally, it was dried in an oven for no less than 24 h.

4. Method 4.

This procedure was used to prepare NBQ-95 in improved yields. To a small round-bottom flask containing 3 mL of DMSO-$d_6$ an egg- or round-shaped stirring bar, are added 0.15-0.3 g-sample of the 2-styrylbenzothiazole (II) to be isomerized. The procedure works well even if the 2-strylbenzothiazole (II) is not completely soluble in DMSO. The flask is placed in a photochemical reactor, such as a Rayonet Apparatus fitted with 350 nm lamps and irradiated with magnetic stirring for a period of 4-6 h. At the end of the reaction period the solid is completely dissolved and solidifies upon cooling to room temperature. The reaction mixture is added to a beaker containing 50-75 mL of distilled water and allowed to stir for an additional 15 min. The precipitated solid is removed by vacuum distillation and washed with three 50-mL portions of distilled water. The solid is placed in a disecator and allowed to dry for a period of 24 h. The solid is dissolved in 100 mL of dry benzene and dried with anhydrous sodium sulfate. The sodium sulfate is removed by filtration and the transparent solution is placed in the irradiation tube and exposed to 350 nm light in a Rayonet Apparatus and worked-up as described in Method 1 for the synthesis of BQS.

After the synthesis of (E)-2-Styrlbenzazlole and Benzazlol [3,2-a]quinolinium Chlorides (BQS) and the inclusion of amino-substituent and nitro-substituent the results of the four selected compounds are:

1. NBQ-38(7-Ethyl-3-nitrobenzimidazolo[3,2-a]quinolinium Chloride)

Following Method 1, 2-(2$^1$-Chloro-5$^1$-nitrostyryl)-1-ethylbenzimidazole (IIt) (0.60 g, 1.8 mmol) was photocyclized (BQS Method 1) to afford 0.45 g (75%) of NBQ-38: $^1$H NMR (DMSO-$d_6$, 300 MHz) δ 9.43 (d, J=9.0 Hz, 1 H, aromatic), 9.40 (d, J=3.0 Hz, 1H), 9.20 (d, J=9.0 Hz, 1H aromatic), 9.06 (d, J=9.0 Hz, 1 H, aromatic), 8.78 (dd, J=9.0, 3.0 Hz, 1 H, aromatic), 8.69 (d, J=9.0 Hz, 1 H aromatic), 8.43 (d, J=9.0 Hz, 1 H aromatic), 8.05-7.94 (m, 2 H, aromatic), 5.01 (q, J=7.5 Hz, 2 H, $CH_2$), 1.50 (t, J=7.5 Hz, 3 H, Me); $^{13}$C NMR (DMSO-$d_6$, 300 MHz) δ 31.3, 111.7, 113.6, 116.4, 118.9, 123.9, 126.2, 126.4, 126.8, 127.6, 128.6, 132.7, 136.1, 139.1, 143.9, 144.8; IR (KBr) 3400.0, 3350.0, 3025.0, 3000.0, 2950.0, 2925.0, 1618.0, 1570.2, 1527.6, 1473.2, 1451.0, 1427.2, 1384.3, 1346.5, 1373.0, 1253.0, 1253.4, 1208.8, 1161.4, 1088.8, 987.0, 913.1, 812.9, 763.2, 737.6, 696.7, 601.7, 584.5, 556.3, 507.4, 455.6 cm$^{-1}$. Compound was analyzed as the perchlorate derivative. Anal Calcd for $C_{17}H_{14}ClN_3O_6$: C, 52.12; H, 3.60; N, 10.73. Found: C, 52.08; H, 3.63; N, 10.67.

2. NBQ-95(2-Chloro-10-methyl-3-nitrobenzothiazolo[3,2-a]quinolinium chloride)

Synthesized by using Method 4 starting from (E)-5-methyl-2-(2,4-dichloro-5-nitrostyryl)benzothiazole (0.543 g, 1.49 mmol), prepared from the condensation of 2,4-dichloro-5-nitrobenzaldehyde and 2,5-dimethylbenzothiazole in boiling acetic anhydride as described in FIG. 3 (BQS Method 1). The resulting styryl derivative (IIc) was photocyclized to give 0.22 g (41%) of NBQ-95 as a yellow solid: mp 236-240° C. (dec.); $^1$HNMR(300.15 MHz, DMSOd$_6$): δ ppm 9.54 (s, 1H), 9.37 (s, 1H), 9.06 (s, 1H), 9.00 (s, 2H), 8.59 and 7.86 (AB, 2H, J=8.4 Hz), 2.74 (s, 3H); UV-vis (95% EtOH) $λ_{max}$/nm (e): 389 (11196), 380 (11363), 270 (14858), 225 sh (21441) and 202 (28390); Anal. Calcd for $C_{16}H_{10}Cl_2N_2O_2S\cdot H_2O$: C, 50.14; H, 3.16; N, 7.31%. Found: C, 49.85; H, 3.35; N, 7.00%.

3. ABQ-38 and ABQ-95(3-amino-7-ethylbenzimidazo[3,2-a]quinolinium chloride, and 3-amino-2-chloro-10-methylbenzothiazolo[3,2-a]quinolinium chloride)

The amino precursors of ABQ-38 and ABQ-95, (E)-7-ethyl-2-(5-amino-2-chlorostyryl)benzimidazole IIv and (E)-5-methyl-2-(5-amino-2,4-dichlorostyryl)benzothiazole IId, respectively, were prepared by the reduction of the corresponding nitro derivatives with hydrazine in the presence of nickel boride in dry methanol, see FIG. 3. (E)-7-ethyl-2-(5-amino-2-chlorostyryl)benzimidazole IIv was photocyclized as described (BQS Method 1) to give 3-amino-7-ethylbenzimidazo[3,2-a]quinolinium chloride (ABQ-38) as a yellow solid: 1H NMR (500.13 MHz, DMSO-d6): δ ppm 9.05 (d, 1H, J=8.50 Hz), 8.88 (d, 1H, J=9.0 Hz), 8.56 (d, 1H, J=9.5 Hz, 8.27 (d, 1H, J=8.5 Hz), 8.23 (d, 1H, J=9.50 Hz), 7.90 (t, 1H, J=7.5 Hz), 7.81 (t, 1H, J=7.5 Hz), 7.43 (dd, 1H, J=8.5, 2.5), 7.27 (d, 1H, J=2.5 Hz), 4.83 (q, 2H, J=7.0 Hz), 1.48 (t, 3H, J=7.0 Hz); UV-vis (95% EtOH) $λ_{max}$/nm (e): 409 (1410), 351 (8104), 336 (9815) and 271 (20866); HRMS calcd for C17H16N3 (compound without the chloride counter ion) 262.1, found by ESI at m/z 261.9. (E)-5-methyl-2-(5-amino-2,4-dichlorostyryl)benzothiazole IId was photocyclized as described (BQS Method 1) to give 3-amino-2-chloro-10-methylbenzothiazolo[3,2-a]quinolinium chloride (ABQ-95) as a yellow solid: 1H NMR (500.13 MHz, DMSO-d6): δ ppm 9.17 (s, 1H), 8.92 (s, 1H), 8.63(AB quartet, 2H, J=9.5 Hz), 8.48 (d, 1H, J=8.5 Hz), 7.76 (d, 1H, J=8.5 Hz), 7.53 (s, 1H), 6.50 (m, 2H), 2.70 (s, 3H); UV-vis (95% EtOH) $λ_{max}$/nm (e): 429 (4417), 380 (10 387), 282 (22 568) and 214(2650); HRMS calcd for $C_{16}H_{12}ClN_2S$ 299.0 (without the chloride counter ion), found by ESI at m/z 299.0 M+.

The inclusion of amino-substituent and nitro-substituent in ring A to the synthesis of (E)-2-Styrlbenzazlole and Benzazlol[3,2-a]quinolinium Chlorides (BQS) results in ABQs and NBQs providing several properties, more particularly exhibiting an increment in the biological activity. For example, the ABQs compounds exhibit (1) intra cellular binding; (2) autofluorescence; (3) cytotoxicity on malignant cells through apoptosis activation mediated by mitochondrial damage and caspases 3 and 7 activation and; (4) cellular organelles binding and damage when tested on a human tumor cell line, the Epidermoid carcinoma A431 cells (ATCC CRL-1555ABQs).

Figure 11:
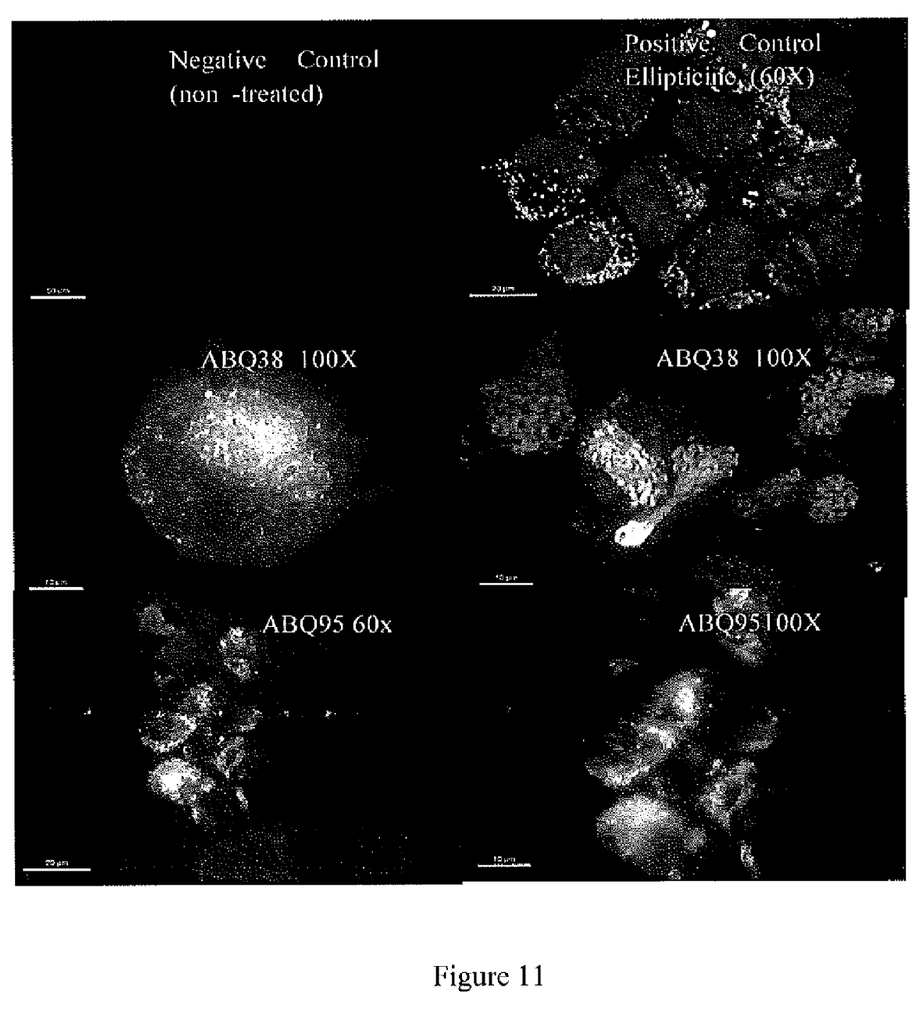
FIG. 11 image of the intra cellular binding of ABQs with Mitochondria and DNA on A431 human tumor.

Regarding the binding on organelles, FIG. 11 shows photos of A431 tumor cells with a Nikon Eclipse E800 wide-field fluorescence microscope with differential interference contrast and motorized stage clearly illustrates the capacity of these ABQs (ABQ-38 and ABQ-95) to bind to DNA and mitochondria.

Figure 12:
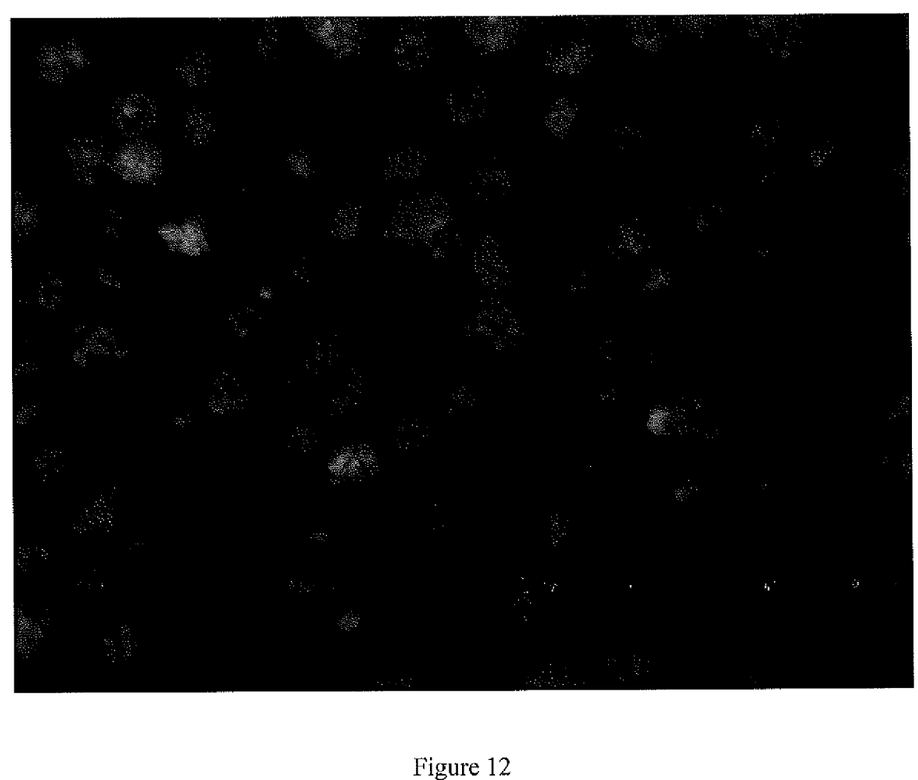
FIG. 12 image of auto fluorescence of ABQ38 on A 431 tumor cells.

Regarding the autofluorencense, Ellipticine was selected as a fluorescent positive control since it is a structural analog of ABQS's. The elipticine's IC50 dose in A431 was determine by treating A431 cell cultures (in duplicates) at concentrations ranging from 0 to 50 µM. The final volume on each plate was 9 mL of modified RPMI 1640 that contained the cell aliquot, media and drug. Cells were exposed to ABQS's and Ellipticine at their IC50 concentrations, incubated and monitored through a 72 hour period by inverted microscopy. An Olympus CKX41 inverted fluorescent microscope (50 w Hg lamp), with U filter; 40× objective. Photographs were obtained at 13-17 seconds of exposure using the Q Capture Software. Auto-fluorescent cells were distinguished from non-auto-fluorescent ones using the negative and positive controls as reference. FIG. 11 and FIG. 12 show auto fluorescence of ABQ38 on A 431 tumor cells with fluorescence microscope (Olympus CKX41). The image clearly shows the auto-fluorescence capacity of the ABQ as a marker of cellular interaction.

Regarding the cytotoxicity, in order to determine the the cell cytotoxicity of the BQS, duplicates cultures of $5 \times 10^6$ cells were seeded in 25 cm² flasks. The final volume on each plate was 9 ml of modified RPMI 1640 that contained the cell aliquot, media and BQS of present invention. Cells were then incubated for 4 hours to allow cells to adhere to the flask. Cells were cultured for 48 hours with BQS at concentration ranging from 5 to 100 uM. A negative control treated with ultra pure water (vehicle) was included in each experiment. Cells in culture were treated with each compound at the different concentration to determine their growth inhibition potency through the determination of the $IC_{50}$ or inhibition of 50% of the cell population. At the end of the exposure period, media was removed and cultures rinsed twice with phosphate buffered saline (PBS) for removal of the compounds in solution. Cells detached with 5% trypsin enzyme, centrifuged, resuspended in fresh media and counted through a cell viability protocol, such as the Trypan Blue Exclusion analysis. Cell survival was calculated and plotted against time with the Microsoft Excel® software. FIG. 12 shows the obtained IC50% of the ABQs in comparison with their nitro substituted analog was as follow: NBQ38: 36 uM; ABQ38: 32 uM; NBQ95: 28 uM and ABQ95: 36 uM.

Regarding the apoptosis induction mediated by membrane permeability and caspases activation the programmed cell death (apoptosis) was verified as the main cell death mechanism using the permeability of the mitochondrial membrane as an indicator. Experiments were performed in duplicates. Cells in culture were exposed to BQs at the IC50 concentrations and incubated for 48 hours. Controls included Valinomycin as positive control (5 uM) and ultrapure water as negative control. At the end of the treatment period cells were washed with PBS, detached with 5% trypsin and centrifuged. Cell aliquots were prepared for each sample and stained for an hour with the Mito PT™ assay (Immunochemistry Technologies LLC) following manufacturer's instructions. Apoptotic (527 nm) and non-apoptotic (590 nm) cells were simultaneously observed by inverted microscopy with the U excitation filter and the 40× objective. Apoptotic cells (green) were distinguished from non apoptotic (reddish-orange) using the negative and positive controls as reference.

Figure 13:
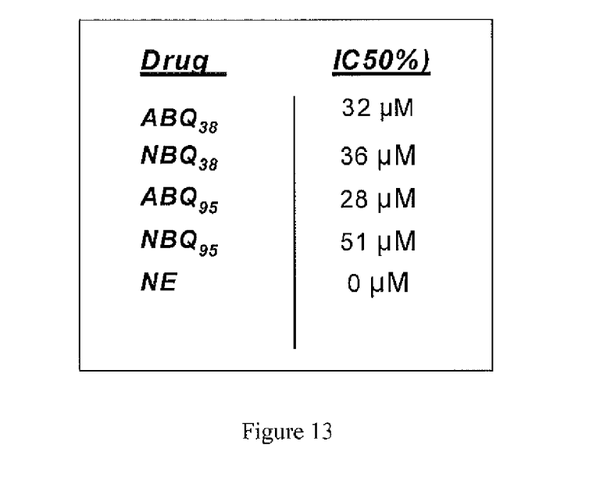
FIG. 13 a table showing determination of the $IC_{50}$ on A431 cells treated with BQs and negative control.
Figure 14:
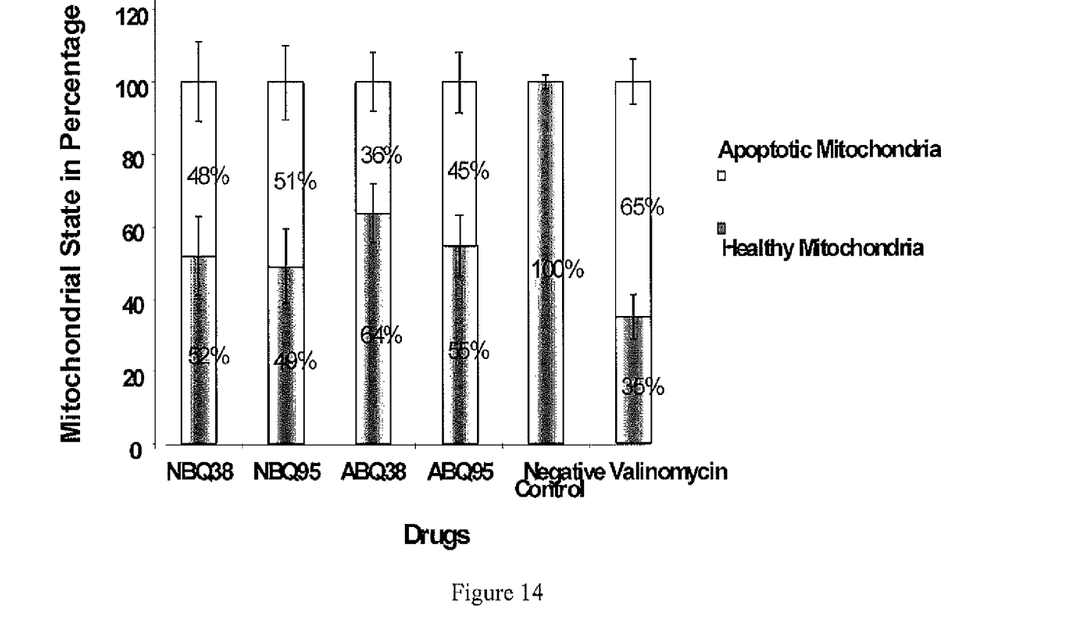
FIG. 14 a graphic showing the state of Mitochondrial Membrane on A431 cells treated with BQs.
Figure 15:
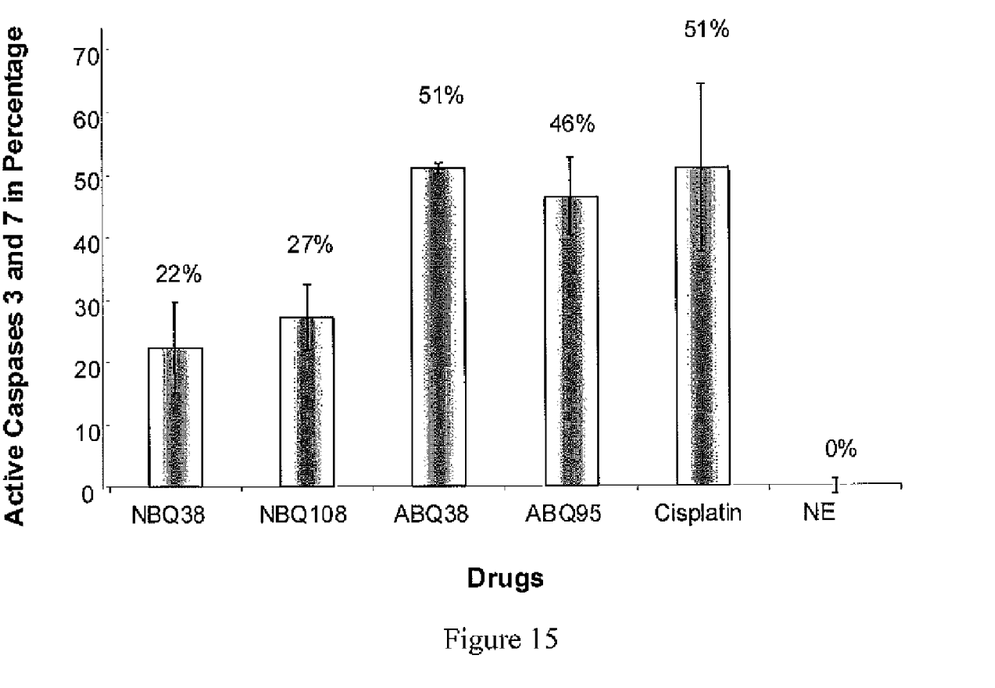
FIG. 15 a graphic showing a comparison of Caspases 3 & 7 activation on A431 cells treated with BQs.

For quantitative apoptosis analysis, aliquots of approximately $5 \times 10^6$ cells after treatment were counted and stained with the Mito PT™ dye. The samples fluorescence was estimated by measuring the fluorescent monomers signal at 527 nm and the J aggregates at 590 nm with a single tube Modulus, Turner Biosystem fluorimeter. The Blue filter captured emissions between 515-570 nm corresponding to apoptotic cells (527 nm) were observed; high fluorescence intensities with this filter revealed damaged mitochondrial membrane. The green filter captured emission ranges of 580-640 nm and detected healthy cells (590 nm); a high fluorescence intensity in this channel revealed healthy mitochondria. Since ABQs weakly emit fluorescence near the emission wavelengths of the fluorochromes, we measured stained and unstained aliquots fluorescence with both filters (blue and green) for background determination and normalization of the data. Data was calculated and normalized twice by subtracting any background fluorescence from the negative control. Percentage of apoptotic cells were calculated and plotted against drugs with Microsoft Excel® software. FIG. 13 illustrates the comparison between the capacity of selected BQS (NBQ-38, ABQ-38, NBQ-95 and ABQ-95) for mitochondria membrane permeability.

Further for caspases 3 and 7 activation a colorimetric assay based on enzyme that binds to active caspases such as Magic Red™ assay from Immunochemistry Technologies was applied. During apoptosis, zymogens that are located on the lysosomes are cleaved becoming DEVDases, the active enzyme of caspases 3 and 7 (Belloc, F. et al 2000). Zymogens are inactive enzyme precursors that require biochemical change (cleavage) to reveal its active site (Biagiotti, E. et al 2000; Lee, B. W., 2003). With the Magic Red™ assay apoptotic cells with inactive caspases 3 and 7 will not fluoresce while cells with active caspases 3 and 7 fluoresces red indicating negative or positive apoptosis. Literature indicates that Staurosporine and Cisplatin induce apoptosis with the involvement of caspases 3 and 7 (Zhang, X. D. et al 2004; Blanc, C. et al 2000) making Cisplatin and Staurosporine appropriate positive controls for this assay.

Cell culture media, such as RPMI 1640, modified with additional nutrients and additives such as Fetal Bovine serum and antibiotic has been added to improve the cell replication and prevent bacterial contamination was employed. Cell cultures of $5 \times 10^6$ cells were seeded on 25 cm² t-flasks (in duplicates). The final volume on each plate was 9 ml of modified RPMI 1640 that contained the cell aliquot, media and drug. Cisplatin (3 uM) and Staurosporine (1 uM) were used as positive controls and non-treated cells as the negative control for apoptosis induction capability. At the end of the treatment time cells were washed with PBS, detached with 5% trypsin enzyme and centrifuged. Cells were counted and aliquots were stained for an hour with cresyl violet (fluorochrome). Active caspases 3 and 7 were monitored qualitatively with inverted microscopy, capturing cell images with the G filter at 9 seconds of exposure with a 40× Objective. Apoptotic cells (red) were distinguished from non apoptotic (non-fluorescent) using the negative and positive controls as reference. Aliquots of exposed cells to the nearest $5 \times 10^5$ were prepared and stained with the dye following the manufacturer's instructions with slight modifications.

As observed on FIG. 12 the order of Caspases 3 and 7 activation was as follows: Cisplatin; 51±13%=ABQ38; 51±1%)>ABQ95; 46±6%>BQ108; 27±5%>NBQ38; 22±7% and Negative Control; 0±1%. ABQ38 presented the highest Caspases 3 and 7 activation at 48 hours of exposure.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patently distinguish any amended claims from any applied prior art.

The invention claimed is:

1. A synthesis procedure for a amino-substituted benzazolo [3,2-a]quinolinium chloride salts compound consisting of wherein R1 is chloride and a amino group, R2 is selected from a group consisting of methyl or hydrogen, and X is selected from a group consisting of sulfur and NR, wherein N is nitrogen and R a general alkyl group; comprising the steps of:
a. synthesis of a nitro substituted 2-(2-chlorostyryl) benzazole;
b. reduction of the nitro group to form an amino-substituted 2-(2-chlorostyryl) benzazole; and
c. photo-induced cyclization procedure of said amino-substituted 2-(2-chlorostyryl) benzazole to generate a biological florescent amino-substituted benzazolo[3,2-a]quinolinium chloride salts, wherein said photo-induced cyclization procedure comprises selecting a vessel permeable to a wavelength of 350 nm and irradiations means, wherein said irradiation mean is equipped with 350 nm wavelength lamps.

2. A synthesis procedure for a amino-substituted benzazolo [3,2-a]quinolinium chloride salts compound as in claim 1 wherein the reduction of nitro group comprises a hydrazine using nickel boride as catalyst.

3. A synthesis procedure for a amino-substituted benzazolo [3,2-a]quinolinium chloride salts compound as in claim 1 wherein the synthesis of a nitro substituted 2-(2-chlorostyryl) benzazole comprises;
a. dissolving in a molar excess of acetic anhydride and refluxed for 18 to 24 h an equimolar mixture, wherein said equimolar mixture consists of a 2-chlorosubstituted benzaldehyde and a 2-methylbenzazole derivatives;
b. allowing said equimolar mixture to cool at a temperature between 23°-25° C. wherein a solid is precipitated; and
c. separating the precipitated solid and exposing said solid to a recrystallization process.

4. A synthesis procedure for a amino-substituted benzazolo [3,2-a]quinolinium chloride salts compound as in claim 3 wherein the precipitated solid is separated through filtering, washed with acetic anhydride, or cold 2:1hexane/acetone mixture.

5. A synthesis procedure for a amino-substituted benzazolo [3,2-a]quinolinium chloride salts compound as in claim 3 wherein the recrystallization process comprises an organic aprotic solvent selected from acetone, hexane/acetone 1:1 mixture, cyclohexane or toluene.

6. A synthesis procedure for a amino-substituted benzazolo [3,2-a]quinolinium chloride salts compound as in claim 1 wherein the synthesis of a nitro substituted 2-(2-chlorostyryl) benzazole comprises;
a. adding an equimolar solution to a 50 percent sodium hydroxide solution with constant stirring at a temperature between 23°-25° C., wherein said equimolar solution consists of a 2-methylbenzazole and a 2-chloro-6-substitutedbenzaldehyde in approximately 10 mL of dimethyl sulfoxide;
b. stirring for an additional 5-15 min said equimolar solution;
c. adding water and stirring for approximately 5 min until a solid precipitates; and
d. separating said precipitated solid and exposing said solid to a recrystallization process.

7. A synthesis procedure for a amino-substituted benzazolo [3,2-a]quinolinium chloride salts compound as in claim 6 wherein the precipitated solid is separated through vacuum filtration.

8. A synthesis procedure for a amino-substituted benzazolo [3,2-a]quinolinium chloride salts compound as in claim 6 wherein the recrystallization process comprises toluene or acetone.

9. A synthesis procedure for a amino-substituted benzazolo [3,2-a]quinolinium chloride salts compound as in claim 6 wherein the step of adding said equimolar mixture comprises reflux said equimolar solution with a small amount of a 2-methylbenzazole derivative in boiling acetic anhydride for a reaction time between 48 to 168 h.

10. A synthesis procedure for a amino-substituted benzazolo[3,2-a]quinolinium chloride salts compound as in claim 1 wherein the synthesis of a nitro substituted 2-(2-chlorostyryl) benzazole comprises the following steps,
a. adding a 2.2 equivalent of NaH in dimethoxyethylene to a portion of (E)-2-Styrlbenzazoleproducing a first reaction mixture;
b. stirring said first reaction mixture at a temperature between 23°-25° C. for 30 min;
c. alkylation with an alkylating agent, wherein said alkylating agent alkyl halide is slowly added at a temperature between 23°-25° C. producing a second reaction mixture, wherein said second reaction mixture consists of 1.5 equivalents of alkylating agent per equivalent of (E)-styrylbenzazole;
d. stirring said second reaction mixture under a nitrogen atmosphere for 6-24 h;
e. cooling said second reaction mixture in an ice-water bath and adding water until a solid precipitates; and
f. filtering said solid precipitation under vacuum, washed using 1:1 acetone/hexane mixture and air-dried.

11. A synthesis procedure for a amino-substituted benzazolo[3,2-a]quinolinium chloride salts compound as in claim 1 wherein the photo-induced cyclization procedure comprises:
a. placing a preferred amount of a (E)-2-(2-chlorostyryl) benzazole inside said vessel; and
b. irradiating said vessel with said irradiation means for a preselected time divided in intervals, wherein each interval the solution is filtered to remove part of a nitro-substituted benzazolo[3,2-a]quinolinium chloride salts compound in a pure form and the rest of said nitro-substituted benzazolo[3,2-a]quinolinium chloride salts compound remained at the vessel walls is extracted.

12. A synthesis procedure for a amino-substituted benzazolo[3,2-a]quinolinium chloride salts compound as in claim 11 wherein said preferred amount placed inside said vessel comprises 0.2-1.0 grams of said (E)-2-(2-chlorostyryl) benzazole dissolved in 150-250 mL of 3:1 benzene: dioxane mixture and said irradiation time is 10-18 hours in intervals of 4-6 hours.

13. A synthesis procedure for a amino-substituted benzazolo[3,2-a]quinolinium chloride salts compound as in claim 11 wherein said preferred amount placed inside said vessel comprises a 0.2-1.0 g of said (E)-2-(2-chlorostyryl) benzazole dissolved in 150-250 mL of 2:1:1 benzene:bromobenzene:dioxane mixture.

14. A synthesis procedure for a amino-substituted benzazolo[3,2-a]quinolinium chloride salts compound as in claim 11 wherein said preferred amount placed inside said vessel comprises a 0.2-1.0 g of said (E)-2-(2-chlorostyryl) benzazole (II) dissolved in 150-250 mL of 3:1 benzene: dioxane mixture, wherein said mixture is first degassed with Argon and then irradiated for 5-18 h in intervals of 4-5 h.

15. A synthesis procedure for a amino-substituted benzazolo[3,2-a]quinolinium chloride salts compound as in claim 11 wherein said nitro-substituted benzazolo[3,2-a]quinolinium chloride salts compound remained at the walls of said vessel is extracted with distilled water and filtered.

16. A synthesis procedure for a amino-substituted benzazolo[3,2-a]quinolinium chloride salts (BQS) compound as in claim 15 wherein said filtered water is subject to freeze-drying to isolate the pure BQS.

17. A synthesis procedure for a amino-substituted benzazolo[3,2-a]quinolinium chloride salts compound as in claim 1 wherein the photo-induced cyclization procedure comprises:
a. filling said flask with a mixture, wherein said mixture comprises 3 mL of methyl sulfoxide;
b. adding a 2-styrylbenzazole to said mixture;
c. placing said flask at said irradiation means, and irradiating the mixture with a magnetic stirring for a period of 4-6 h, until a solid is completely dissolved and solidifies at a temperature between 23°-25° C. generating a reaction mixture;
d. adding said reaction mixture to a beaker containing 50-75 mL of distilled water and stirring for approximately 15 min until a first solid is precipitated;
e. removing the first precipitated solid and placing said first precipitated solid in a desicator;
f. allowing the first precipitated solid to dry for a selected time; and
g. dissolving said first precipitated solid in 100 mL of dry benzene and drying said second solid.

18. A synthesis procedure for a amino-substituted benzazolo[3,2-a]quinolinium chloride salts compound as in claim 17 wherein said selected time is 24 hours and after dissolving said first precipitated solid in 100 ml of dry benzene is dried with anhydrous sodium sulfate.

19. A synthesis procedure for a amino-substituted benzazolo[3,2-a]quinolinium chloride salts compound as in claim 18 wherein after drying said precipitated solid said sodium sulfate is removed by filtration and the resultant solution is placed in a irradiation vessel and exposed to 350 nm light at said irradiation means.

20. A synthesis procedure for a amino-substituted benzazolo[3,2-a]quinolinium chloride salts compound as in claim 17 wherein removing said first precipitated solid comprises removing said first precipitated solid by vacuum distillation and washing said first precipitated solid with distilled water.

21. A synthesis procedure for a amino-substituted benzazolo[3,2-a]quinolinium chloride salts compound as in claim 17 wherein said mixture placed in the flask comprises 0.15-0.3 g of the 2-styrylbenzazole to be isomerized.

* * * * *